(12) United States Patent
Celentano et al.

(10) Patent No.: US 6,172,751 B1
(45) Date of Patent: Jan. 9, 2001

(54) HIGH EFFICIENCY REFLECTOMETRY ILLUMINATOR AND COLLECTOR SYSTEM

(75) Inventors: Mike Celentano; Chris Zachidny, both of Indianapolis, IN (US)

(73) Assignee: UMM Electronics, Inc., Indianapolis, IN (US)

( * ) Notice: Under 35 U.S.C. 154(b), the term of this patent shall be extended for 0 days.

(21) Appl. No.: 09/240,748

(22) Filed: Jan. 29, 1999

Related U.S. Application Data

(60) Provisional application No. 60/073,226, filed on Jan. 30, 1998.

(51) Int. Cl.[7] .................................. G01J 3/42; G02B 5/04
(52) U.S. Cl. .............................................. 356/319; 359/833
(58) Field of Search ..................... 356/445, 446, 356/371, 237.2, 319; 359/833, 834

(56) References Cited

U.S. PATENT DOCUMENTS

| | | | |
|---|---|---|---|
| 3,759,607 | * 9/1973 | Boyle | 350/293 |
| 4,853,542 | * 8/1989 | Milosevic et al. | 356/446 |
| 5,309,339 | * 5/1994 | Webb | 356/446 |

* cited by examiner

Primary Examiner—Frank G. Font
Assistant Examiner—Zandra V. Smith
(74) Attorney, Agent, or Firm—Woodard, Emhardt, Naughton, Moriarty & McNett

(57) ABSTRACT

A reflector for improving the signal of spectrophotometer, the reflector comprising a truncated cone having a reflective inner surface and a conical axis, the truncated cone open at a larger axial end thereof, open at a smaller axial end thereof, and having an opening in the cone surface. The reflector returns specularly scattered light back to the surface of a sample, and therefore enhances the amount of collected light.

6 Claims, 5 Drawing Sheets

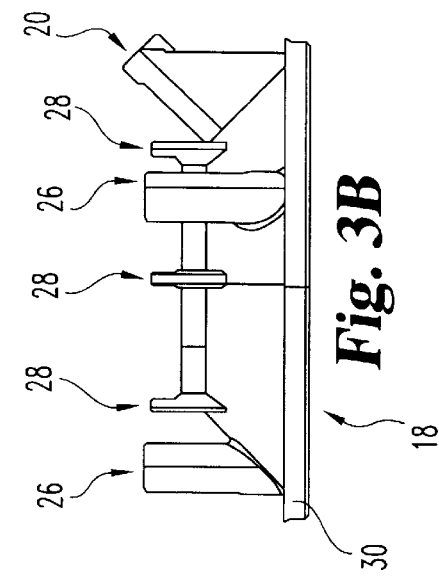
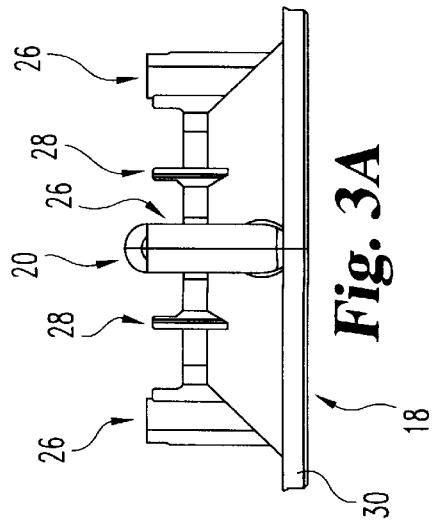
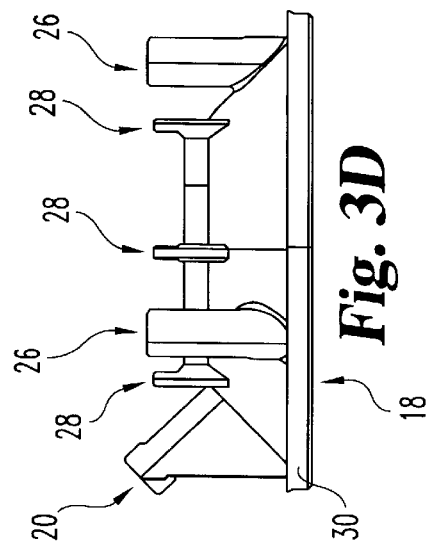
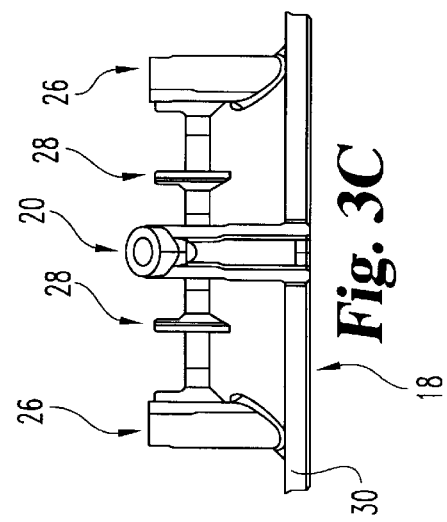

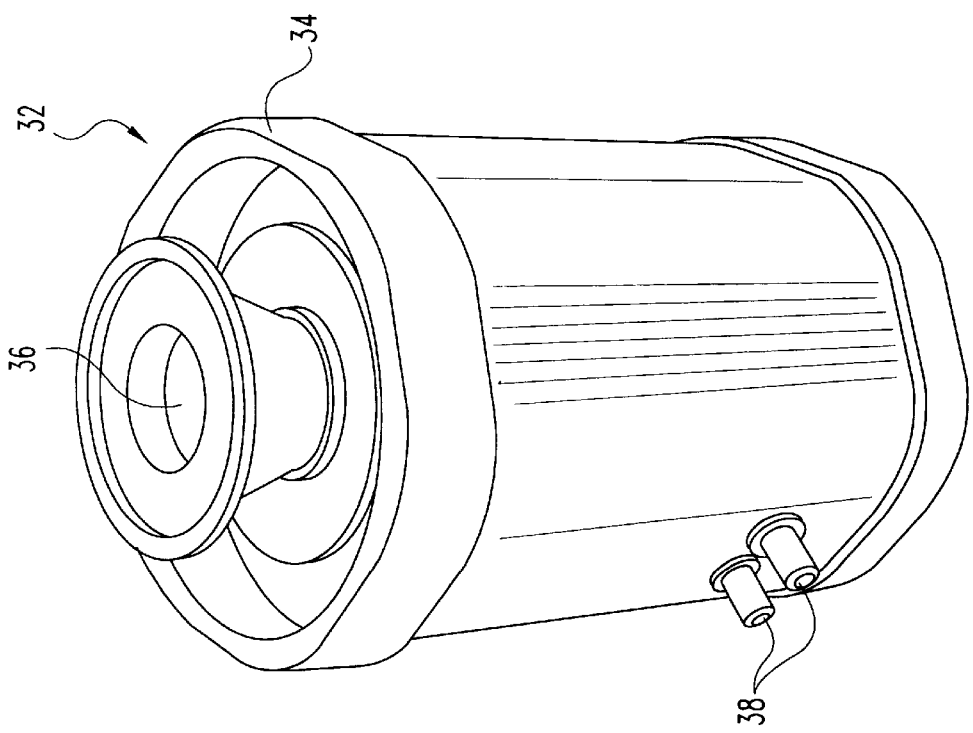
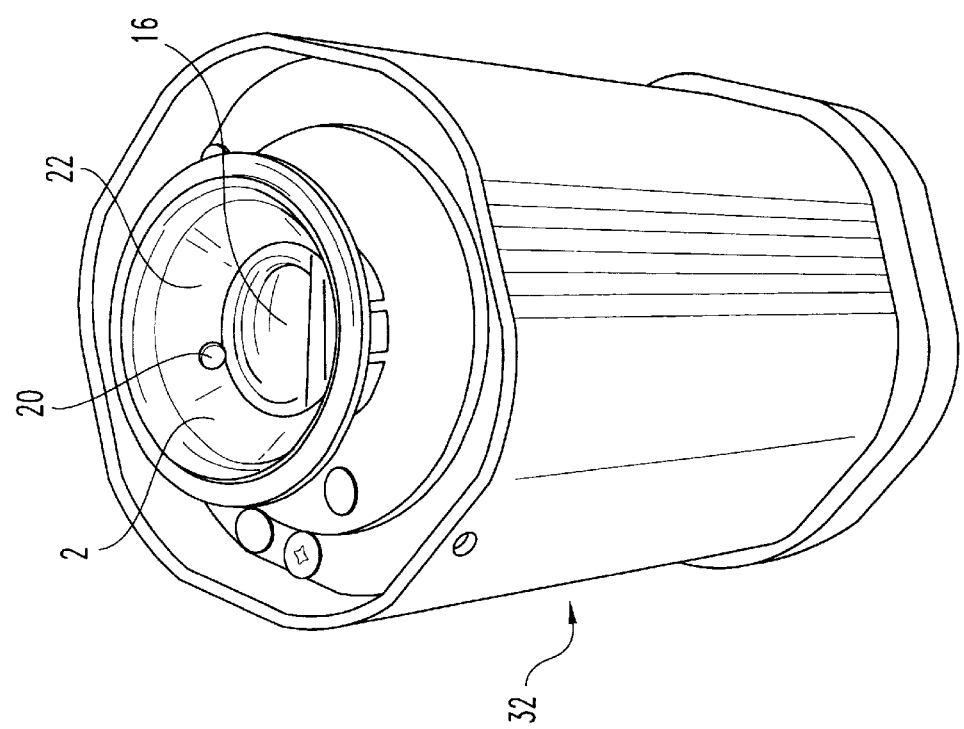

HIGH EFFICIENCY REFLECTOMETRY ILLUMINATOR AND COLLECTOR SYSTEM

This application claims benefit to U.S. Provisional application Ser. No. 60/073,226, filed Jan. 30, 1998.

BACKGROUND OF THE INVENTION

1. Field of the Invention

The present invention relates to a high efficiency reflectometry illuminator collector system.

2. Discussion of the Background

Spectrophotometers may be used to measure the color spectrum on the surface of objects, such as paper, paint chips or fabric swatches. A spectrophotometer for reflectance spectrometry usually includes a light source, such as a light bulb and a power source, optics for transferring the light from the light source to the sample, such as fiber optics, lenses and/or mirrors, and optics for collecting the light, which may also include fiber optics, lenses and/or mirrors. The collected light is then transferred to a device for separating the light into its component wavelengths, such as a diffraction grading or a prism, and then to a detector to measure the intensity of one or more of the different wavelengths of the light. As a reference the intensity of one or more of the different wavelengths of the light. As a reference, the intensity of light generated by the light source may also be transferred by optics to a detector. The signal generated by the detector from the sample light, and the signal generated by the detector from the reference light, may be transferred through a data processing system, such as a computer, and the result displayed or stored. A large variety of configurations and methods are known, and are described in U.S. Pat. Nos. 5,701,175; 5,400,138; 5,319,437; 4,773,761; 3,885,878; and 3,806,256; all of which are incorporated by reference.

A typical geometry of optics closest to a sample in the directive (as opposed to integrating sphere) reflectometry industry includes illumination and collection sections, each with a specific angle from the normal to the sample surface, for example illumination at 45° to the normal of the plane of the sample surface, and collection normal to the surface of the sample. With the exception of highly mirrored samples, all reflectance samples scatter light from the illuminator at various solid angles into the space above the sample. Only a portion of the scattered light is therefore collected by the collection optics, due to the collection angle. It would be desirable, therefore, to use this wasted scattered light, in order to boost the strength of the signal and improve the accuracy and precision of the spectrophotometer.

SUMMARY OF THE INVENTION

Accordingly, one object of the invention is to provide a novel illuminator and collector system to increase the efficiency of the spectrophotometer.

Another object of the invention is to provide a novel spectrophotometer which uses this illuminator and collector system.

Another object of the invention is to provide a novel reflectometry method having improved efficiency.

These objects may be achieved with a novel reflector, comprising: a truncated cone having a reflective inner surface and a conical axis, with an opening at a larger axial end of the truncated cone, an opening at a smaller axial end of the truncated cone, and an opening in the cone surface.

These objects may also be achieved with a spectrophotometer comprising this novel reflector. Furthermore, the objects may also be achieved by a method of measuring the reflectance spectrum of a surface, comprising: illuminating a surface with light at an angle greater than 0 from the normal of the plane of the surface, thereby generating reflected light normal to the plane and other reflected light; reflecting a portion of the other reflected light back to the surface at the angle, thereby generating additional reflected light normal to the plane.

If one form of the invention, a reflector is disclosed, comprising a truncated cone, comprising a cone body defining an outer surface, a reflective inner surface and a conical axis; a first opening at a larger axial end of the cone body; a second opening at a smaller axial end of the cone body; and a third opening through the reflective inner surface between the first and second openings.

In another form of the invention, a spectrophotometer is disclosed, comprising a truncated cone, comprising a cone body defining an outer surface, a reflective inner surface and a conical axis; a first opening at a larger axial end of the cone body; a second opening at a smaller axial end of the cone body; a third opening through the reflective inner surface between the first and second openings; a source of light positioned to emit light rays through the third opening; and a light collector positioned to receive light rays reflected through the second opening.

In another form of the invention, a method for measuring the reflectance spectrum of a surface is disclosed, comprising the steps illuminating a surface with light at an angle greater than 0° from the normal of the plane of the surface, thereby generating reflected light normal to the plane and other reflected light; reflecting a portion of the other reflected light back to the surface at the angle greater than 0° from the normal of the plane of the surface, thereby generating additional reflected light normal to the plane.

In another form of the invention, a spectrophotometer is disclosed, comprising a light source, optics for transferring light from the light source to a sample, optics for collecting light reflected from the surface of the sample, and a detector for detecting the intensity of light reflected from the sample, the improvement comprising a reflector, the reflector comprising a truncated cone, comprising a cone body defining an outer surface, a reflective inner surface and a conical axis; a first opening at a larger axial end of the cone body; a second opening at a smaller axial end of the cone body; and a third opening through the reflective inner surface between the first and second openings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3A illustrates a first side view of the preferred embodiment reflector of the present invention;

FIG. 3B illustrates a second side view of the preferred embodiment reflector of the present invention;

FIG. 3C illustrates a third side view of the preferred embodiment reflector of the present invention;

FIG. 3D illustrates a fourth side view of the preferred embodiment reflector of the present invention;

FIG. 5A illustrates the preferred embodiment reflector of the present invention in a search unit with the search unit fully assembled; and FIG. 5B illustrates the preferred embodiment reflector of the present invention in a search unit with the reflector exposed.

DETAILED DESCRIPTION OF THE PREFERRED EMBODIMENT

Figure 1:
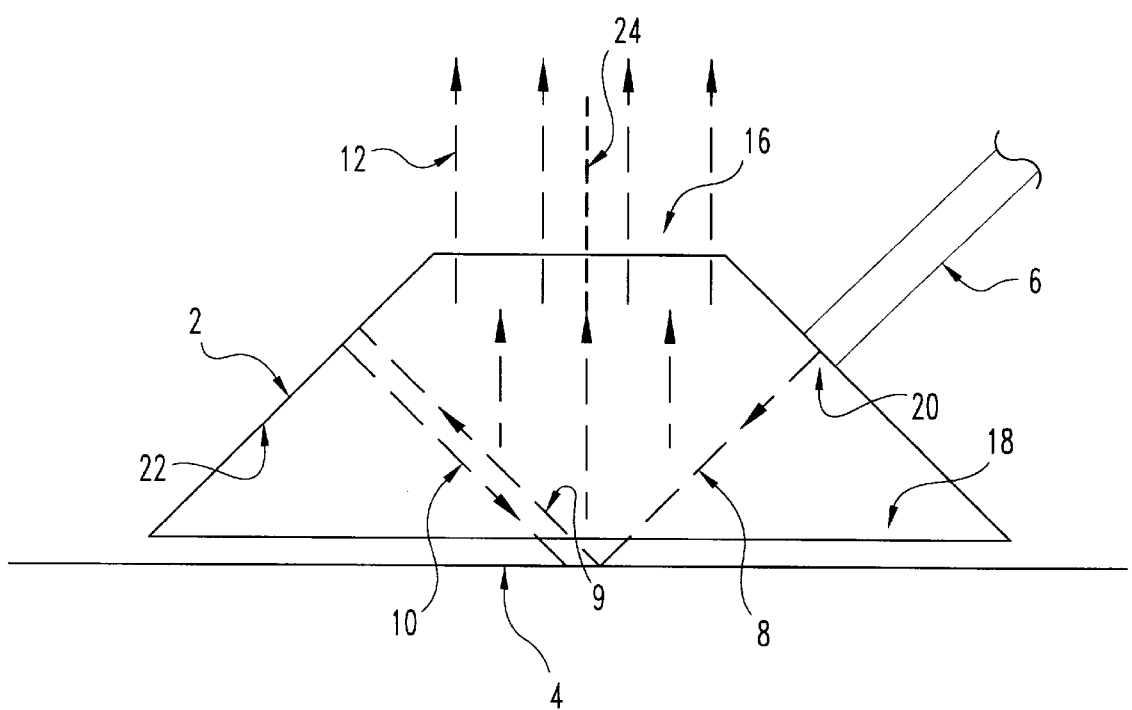
FIG. 1 illustrates a reflector of the present invention showing the path of light from the illuminator, the path of light reflected from the reflector, and the path of light collected by the collector.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

In attempting to produce a high efficiency reflectometry illuminator and collector system, the present inventors considered a variety of different systems. One system considered was a light ring composed of fiberoptic system for collecting the wasted light reflected from the sample, and returning it back to the sample at the appropriate illumination angle. However, it was discovered that this fiberoptic system loses much more light than expected. The present inventors also considered using an integrating sphere to collect and return wasted light back to the sample. However, the light returned to the sample by an integrating sphere is not at the appropriate angle, and therefore does not meet the specific requirements of illumination and detection angle required during precision reflectometry. The inventors also considered using an integrating sphere-type arrangement to collect and redirect all the wasted light back at the sample at the correct illumination angle, however, this system was much too complicated and not practical.

The reflector of the present invention is convenient and practical. The reflector does not collect all of the light reflected from a sample that does not enter the collector, but rather reflects primarily specularly reflected light (light reflected from the sample at the same angle with respect to the normal of the plane of the surface of the sample as the illuminating light). Since most of the wasted light reflected from the sample is specularly reflected, returning this light back to the sample greatly enhances the efficiency of the illumination and collection system.

FIG. 1 schematically illustrates an embodiment of the present invention. The conic reflector 2 has a reflective inner surface 22. The conic reflector has a frutoconical shape (i.e. the shape of a truncated cone), and has a conical axis 24, with an opening at the larger axial end 18, and an opening at the smaller axial end 16. In addition, there is an opening 20 in the cone surface 22 of the reflector 2. Also illustrated is an illuminator 6, a sample 4, and a collector 14. Light passes through the illuminator 6, such a fiber optics, through the opening 20 in the cone surface 22 and reaches the sample 4 along light path 8. Some of the light is reflected normal to the surface of the sample (along the conical axis 24) and reaches the collector 14 as collected light 12. Other light 9 is specularly reflected towards the inner surface 22 of the conic reflector 2, reflects off the inner surface 22 of the reflector 2, and returns as recycled light 10 back to the sample 4. Some of this recycled light 10 is then reflected along the normal of the surface (i.e. the conical axis 24) of the sample 4 and becomes additional collected light 12.

Figure 2A:
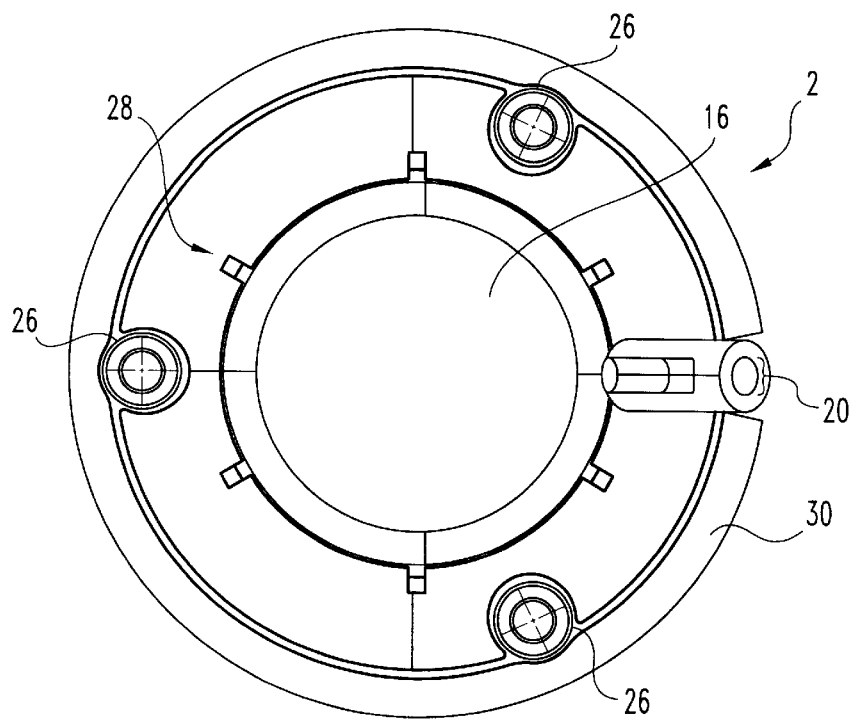
FIG. 2A illustrates a schematic top view of a preferred embodiment reflector of the present invention.
Figure 2B:
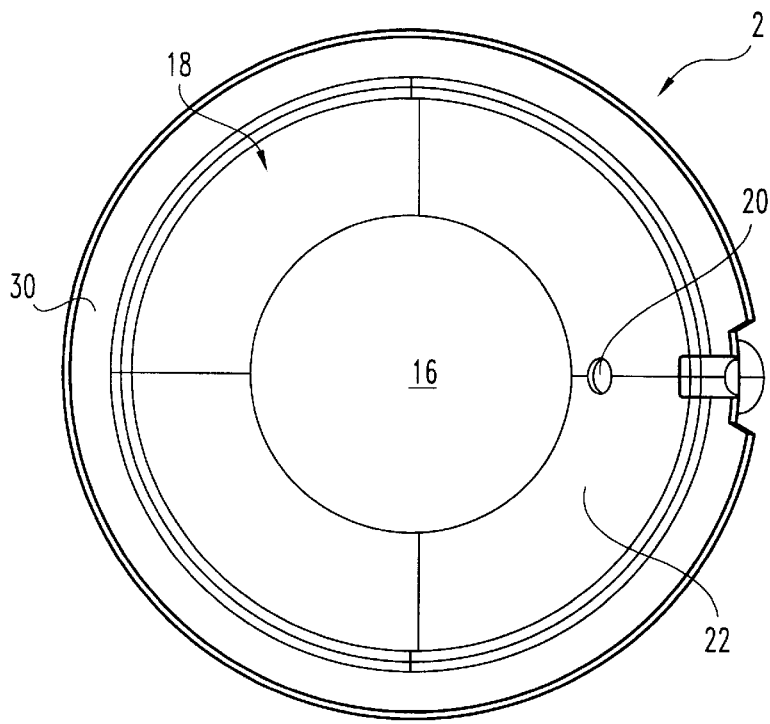
FIG. 2B illustrates a bottom view of a preferred embodiment reflector of the present invention.
Figure 4A:
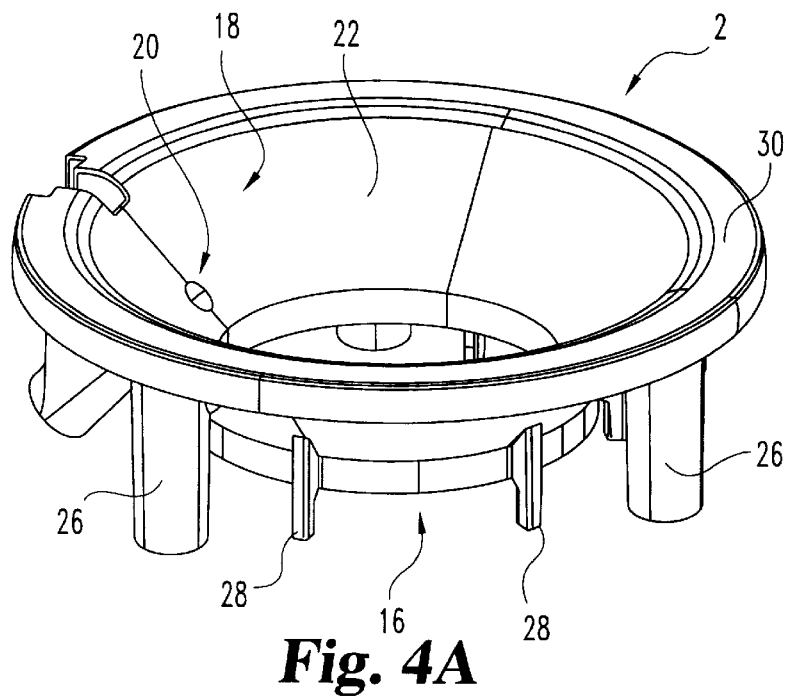
FIG. 4A illustrates an inclined bottom view of the preferred embodiment reflector of the present invention.
Figure 4B:
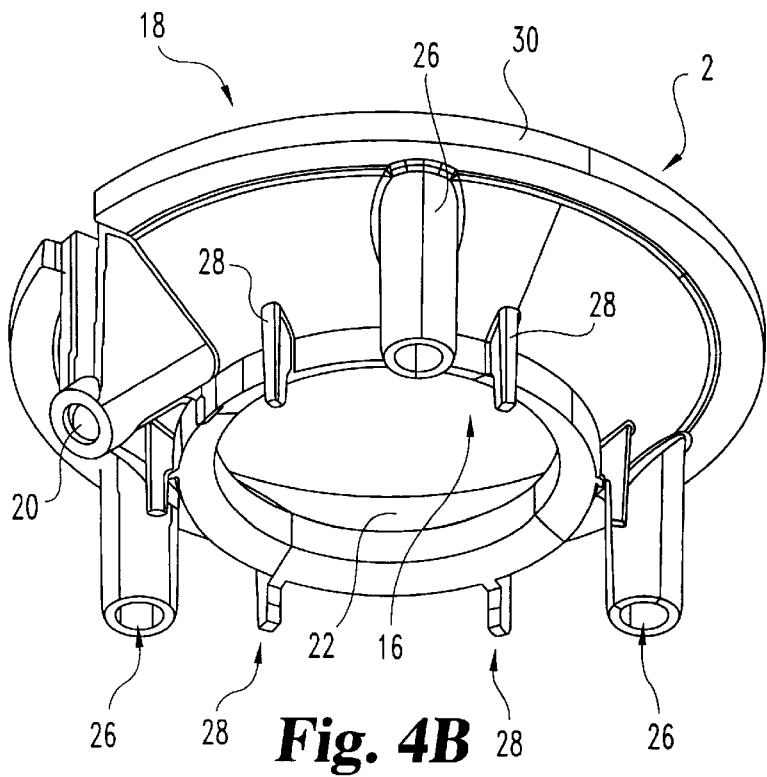
FIG. 4B illustrates an inclined top view of the preferred embodiment of the present invention.

FIG. 2 illustrates a top view (A) and a bottom view (B) of the preferred embodiment reflector 2 of the present invention. In addition to the parts illustrated in FIG. 1, FIG. 2 also illustrates optional mountings 26, optional supports 28 (only one support is labeled) and an upper lip 30 of the reflector 2. FIGS. 3A–D show four different side views of the reflector 2, while FIG. 4 shows an angled view of the bottom of the reflector (A) and an angled view of the top of the reflector (B). In practice, the sample 4 will be placed upon the lip 30 or, alternatively, a sample holder (not shown) will be placed upon the lip 30, wherein the sample holder positions the sample 4 at the conical axis 24. The collector 14 will comprise an optical system which collects light reflected from the sample 4 through the opening 16 for subsequent analysis. The sample 4 is illuminated by means of light projecting through the opening 20. Because of the mirrored surface of the inner cone surface 22, any specular reflection of light from the sample 4 that is not received by the collector 14 is not wasted, but is rather reflected back to the sample 4 until it is eventually reflected along the conical axis 24 to the collector 14. Because of the low loss of the mirrored surface 22, the efficiency of the reflector 2 of the present invention in collecting the light emitted through the opening 20 at the collector 14 is greatly improved.

FIG. 5 illustrates a search unit 32, fully assembled (B) or with the top removed (A). The search unit 32 includes a top 34, having an opening 36 therein. The search unit 32 also has two light ports 38 through which light may enter to illuminate the sample, and through which collected light exits back to the main body of the spectrophotometer. Not visible in the illustration is the internal fiber optic channel which transfers light from one of the light ports 38 (the input light port) to the opening 20 in the cone surface, nor the optical system for transferring light from the smaller axial opening 16 of the reflector 2, which includes a lens (lens collection area) to the other (output) light port 38.

The reflector 2 of the present invention may be made from almost any material, but preferably an easily molded material such as ABS plastic or its functional equivalent. Injection molding using ABS is preferred because it is a low cost process, gives smooth surfaces and produces a reflector 2 with high durability. The inner surface 22 of the reflector 2 should be metalized to a near mirror finish. Metalization is a very important step; the resulting finish must be very smooth and free from dirt, dust and globs of metal. All cavities must be blocked prior to metalization. Preferably the cone angle ø of the truncated cone (two times the angle between the conical axis 24 and the line along the conical surface 22), is preferably $2 \cdot (90° - \theta)$, where $\theta$ is the angle of illumination of the sample 4 with respect to the conical axis 24 (i.e., the angle between the light path 8 and the conical axis 24). A deviation of ±10° from these preferred values is possible.

The illuminator 6 is typically made of fiber optics, and transfers light from the light source through the opening 20 in the cone surface 22, to illuminate the sample 4. Preferably, the fiber optics are made from acrylic, which results in a cone of light having a cone angle of about 30°.

Glass may also be used for the fiber optics, but results in a cone of light having a cone angle of about 60°. The term "substantially parallel light rays" means a cone of light having a cone angle of about 30°. The optics used to transfer the light from the light source to the sample, and collected light from the sample to the detector, may include fiber optics, as well as other optical components such as lenses. The light source, the optics for transferring the light to the sample and capturing the collected light, separating the light into its component wavelengths, detecting the intensity of the various wavelengths, and manipulating the resulting signal for display or storage, are well known to those of ordinary skill in the art.

The optional mountings 26 and supports 28 are adapted so that the reflector 2 may be attached to a light collecting device, such as a search unit 34, and will vary depending upon the particular application.

Obviously, numerous modification and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A reflector, comprising:
    a truncated cone, comprising:
        a cone body defining an outer surface, a reflective inner surface and a conical axis;
        a first opening at a larger axial end of the cone body;
        a second opening at a smaller axial end of the cone body; and
        a third opening through the reflective inner surface between the first and second openings.

2. The reflector of claim 1, further comprising at least one mounting coupled to the cone body for coupling the reflector to a light collecting device.

3. A spectrophotometer comprising
    a truncated cone, comprising:
        a cone body defining an outer surface, a reflective inner surface and a conical axis;
        a first opening at a larger axial end of the cone body;
        a second opening at a smaller axial end of the cone body;
        a third opening through the reflective inner surface between the first and second openings;
        a source of light positioned to emit light rays through the third opening; and
    a light collector positioned to receive light rays reflected through the second opening.

4. The spectrophotometer of claim 3, wherein the source of light produces substantially parallel light rays directed substantially to a point of intersection of the conical axis with a plane formed by the first opening at the larger axial end.

5. The spectrophotometer of claim 4, wherein the substantially parallel light rays are directed substantially perpendicular to the inner surface of the truncated cone.

6. In a spectrophotometer, having a light source, optics for transferring light from the light source to a sample, optics for collecting light reflected from the surface of the sample, and a detector for detecting the intensity of light reflected from the sample, the improvement comprising a reflector, the reflector comprising:
    a truncated cone, comprising:
        a cone body defining an outer surface, a reflective inner surface and a conical axis;
        a first opening at a larger axial end of the cone body;
        a second opening at a smaller axial end of the cone body; and
        a third opening through the reflective inner surface between the first and second openings.

* * * * *